United States Patent [19]

Orban et al.

[11] Patent Number: 5,436,322
[45] Date of Patent: Jul. 25, 1995

[54] AZO COUPLING OF 2-NITROANILINES WITH 2,4,-DISBUSTITUTED PHENOLS

[75] Inventors: Ivan Orban, Basel; Martin Holer, Magden, both of Switzerland

[73] Assignee: Ciba-Geigy Corporation, Ardsley, N.Y.

[21] Appl. No.: 304,452

[22] Filed: Sep. 12, 1994

[30] Foreign Application Priority Data

Sep. 16, 1993 [CH] Switzerland ............... 2787/93

[51] Int. Cl.6 ............... C09B 41/00; C07D 249/20
[52] U.S. Cl. ............... 534/581; 534/843; 548/260
[58] Field of Search ............ 534/581, 843; 548/260

[56] References Cited

U.S. PATENT DOCUMENTS 3,998,804 12/1976 Rody et al. ............ 260/206
4,891,424 1/1990 Seltzer et al. ............ 534/581 X

OTHER PUBLICATIONS

Derwent Abst. 35772 A/20 of JP 53-37628 Apr. 6, 1978.
Chem. Abst. 94: 30333 (1980).

*Primary Examiner*—Robert W. Ramsuer
*Assistant Examiner*—Fiona T. Powers
*Attorney, Agent, or Firm*—Michele A. Kovaleski

[57] ABSTRACT

A process for the preparation of compounds of the formula I is described

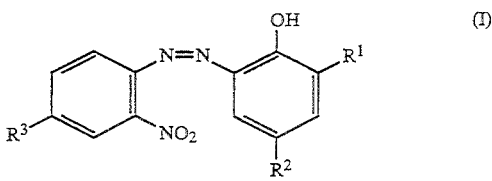

in which $R^1$ and $R^2$ independently of one another are $C_1$-$C_7$alkyl; and $R^3$ is hydrogen or halogen, by reaction of a diazonium salt of a 2-nitroaniline in acid aqueous solution with a phenol dispersed in water.

The process comprises employing as the dispersant a $C_8$-$C_{20}$alkanesulfonic acid or a corresponding alkanesulfonate or a mixture of sulfonic acid and sulfonate together with a polyvinyl alcohol.

The resulting compounds of the formula I can advantageously be reacted further to give benzotriazoles of the formula V

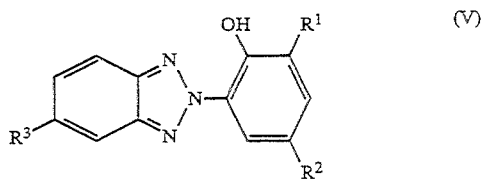

which are used as light stabilizers.

10 Claims, No Drawings

AZO COUPLING OF 2-NITROANILINES WITH 2,4,-DISBUSTITUTED PHENOLS

The invention relates to an improved process for the preparation of azo compounds by coupling a diazotized o-nitroaniline and a sparingly water-soluble 2,4-disubstituted phenol coupling of 2-nitroanilines with 2,4-disubstituted phenols in acid aqueous dispersion, and to an improved process for the preparation of corresponding benzotriazoles starting from diazotized o-nitroaniline and 2,4-disubstituted phenol.

Because of the low solubility of 2,4-disubstituted phenols in water, azo coupling of such compounds has hitherto usually been carried out in the presence of organic solvents and, where appropriate, with the additional addition of surfactants; examples of such processes are to be found, for example, in Derwent Abstr. 35772A/20, and Chem. Abstr. 94, 30333.

U.S. Pat. No. 3,998,804 describes a coupling process of 2-nitroanilines with 2,4-disubstituted phenols in which dispersion of the reactants in water is achieved by addition of about 50% by weight of arylsulfonic acids and sulfonates mixed with polyglycol ethers, based on the phenol employed.

It has now been found that, surprisingly, instead of the known dispersant systems, a mixture of alkanesulfonic acid or corresponding alkanesulfonate and a polyvinyl alcohol can advantageously be employed. By using the dispersant according to the invention, the amount of dispersant required can be reduced significantly compared with the known processes; at the same time, the desired product is obtained with a good yield and in a high purity.

The invention therefore relates to a process for the preparation of compounds of the formula I

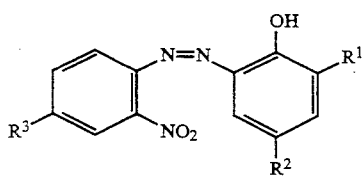

in which $R^1$ and $R^2$ independently of one another are $C_1$–$C_7$alkyl; and $R^3$ is hydrogen or halogen, by reaction of a diazonium salt of a 2-nitroaniline of the formula II

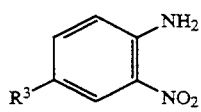

in acid aqueous solution with a phenol of the formula III

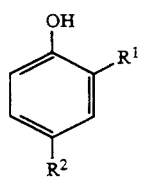

dispersed in water.

The process comprises employing as the dispersant a $C_8$–$C_{20}$alkanesulfonic acid or a corresponding alkanesulfonate or a mixture of sulfonic acid and sulfonate together with a polyvinyl alcohol.

The radicals $R^3$ in formula II and $R^1$ and $R^2$ in formula III here are as defined for formula I.

Preferably, compounds of the formula I in which $R^1$ and $R^2$ independently of one another are $C_1$–$C_5$alkyl and $R^3$ is hydrogen or chlorine, are prepared.

Halogen is —F, —Cl, —Br or —I; in all the embodiments of the invention, a halogen substituent is preferably —Cl or—Br; in particular —Cl.

Alkyl $R^1$ and $R^2$ independently of one another are, within the context of their stated definitions, methyl, ethyl, propyl, butyl, pentyl, hexyl or heptyl; preferred radicals are methyl and branched $C_3$–$C_7$alkyl, for example $C_3$–$C_5$alkyl, in particular tert-butyl. Particularly preferably, one of the two radicals $R^1$ and $R^2$ is methyl or branched $C_3$–$C_5$alkyl and the other radical is branched $C_3$–$C_5$alkyl. Examples of branched $C_3$–$C_5$alkyl are isopropyl, sec-butyl, tert-butyl or tert-amyl (=1,1-dimethylpropyl). Particularly preferred compounds in the process according to the invention are those in which the two radicals $R^1$ and $R^2$ are branched $C_3$–$C_5$alkyl, in particular tert-butyl.

The alkanesulfonic acid which can be employed according to the invention is of the formula IV

in which $R^5$ is $C_8$–$C_{20}$alkyl, in particular $C_{13}$–$C_{17}$alkyl.

Alkanesulfonates, for example alkali metal salts of the acids, such as the lithium, sodium or potassium salt, can be employed in the process according to the invention with the same success as the acids of the formula IV. The acid or sodium or potassium salt are preferably used, and the sodium salt is particularly preferred. Mixtures of the acids and salts mentioned can also be employed.

$R^5$ in formula IV can be a branched or a linear alkyl radical; however, alkanesulfonic acids or alkanesulfonates having linear (=straight-chain) alkyl radicals are of particular practical importance, these being distinguished by their good degradability from an ecological aspect, in addition to their good properties as a dispersant.

The polyvinyl alcohol is essentially composed of recurring units of the formula —$CH_2$—CH(OH)—; the end groups are usually present as free and sometimes also as acetylated OH groups. In principle, however, the nature of the end groups of the polyvinyl alcohol in the process according to the invention is of minor importance. The polyvinyl alcohol to be used according to the invention can also comprise a smaller proportion of units other than those of the formula —$CH_2$—CH(OH)—, for example up to 20%; these can be, for example, ethylene units or those of the formula —CH=CH—, and the polyvinyl alcohol to be used according to the invention is often partly acetylated, i.e. it comprises units of the acetyloxyethylene type.

The molecular weight $M_w$ of the polyvinyl alcohol to be used according to the invention is in general between 10,000 and 250,000, for example between 15,000 and 200,000; a polyvinyl alcohol which has a molecular weight $M_w$ of between 20,000 and 150,000, in particular between 30,000 and 70,000, is preferably employed.

The invention separately relates to the use of $C_8$–$C_{20}$ alkanesulfonic acids and/or corresponding alkanesulfonates together with polyvinyl alcohol as a dispersant during acid azo coupling of 2,4-disubstituted phenols.

The minimum amount of dispersant is in general about 0.5% by weight, in each case based on the theoretically prepared amount of compound of the formula I. The upper limit of dispersant which can be employed according to the invention is essentially determined by economic and ecological expediency; particularly preferably, about 1 to 5 parts by weight of dispersant are employed per 100 parts by weight of azo compound which can be achieved with complete conversion; however, considerably larger amounts, for example up to 20 parts by weight, of dispersant can also be employed. The mixing ratio of alkanesulfonic acid or alkanesulfonate to polyvinyl alcohol can be, for example, between 1:2 and 10:1; however, the dispersant mixture preferably comprises more alkanesulfonic acid or alkanesulfonate than polyvinyl alcohol, so that the mixing ratio of alkanesulfonic acid or alkanesulfonate to polyvinyl alcohol is, in particular, between about 1:1 and 8:1, especially between 1.5:1 and 5:1.

In general 0.5 to 10% by weight, in particular 0.6 to 5% by weight, of alkanesulfonic acid or alkanesulfonate and 0.1 to 5% by weight, in particular 0.15 to 3% by weight, of polyvinyl alcohol, based on the theoretical amount of azo compound, are employed in the process according to the invention.

A process in which 0.8 to 3% by weight of alkanesulfonic acid or alkanesulfonate and 0.2 to 2% by weight of polyvinyl alcohol, based on the theoretical amount of azo compound of the formula I, are employed is of particular industrial interest.

The preparation of the diazonium salt from the compound of the formula II is known to the expert. The resulting aqueous solution of the diazonium salt (diazo solution) usually has a pH of less than 2. Further reaction with the compound of the formula III (azo coupling) is also known per se. A description of the known process is to be found, for example, in the abovementioned U.S. Pat. No. 3 998 804. The process can be summarized in its known steps as follows: in general, nitroaniline of the formula II is first converted into the diazonium salt by reaction with nitrite in aqueous acid, while cooling (diazotization). The nitrite-free solution of this salt (diazo solution) is then reacted with the phenol of the formula III to give the azo compound of the formula I.

The phenols of the formula III are employed in the process according to the invention as dispersions in water. In the present invention, any fine distribution of the phenol in water is described as a dispersion; the phenol of the formula III can be liquid or solid here.

However, at the start of the reaction, not necessarily all the phenol has to be present as a dispersion; it is also possible for some of the phenol still to be present in a non-dispersed form, preferably a liquid form, at this point in time and to be converted into the form dispersed in water only during the reaction. The term "dispersed phenols" in the present Application therefore also includes those phenols which are only partly present in disperse distribution in water. Emulsions are preferred in the process according to the invention.

The dispersions can be prepared, for example, by addition of the alkanesulfonic acid or alkanesulfonate and polyvinyl alcohol dispersants according to the invention to the phenol, in particular to the liquid phenol, and subsequent addition of water, or by addition to the phenol/water mixture. Preferably, the dispersion of phenol of the formula III, water and dispersant mixture is prepared by dissolving the alkanesulfonic acid or the alkanesulfonate and the polyvinyl alcohol in water and mixing the resulting solution with the phenol of the formula III. Both the dissolving operation and the mixing operation are advantageously carried out with heating, for example to 30° to 80° C., during which the phenol is preferably melted, and intensive thorough mixing.

The ratio of the amounts of water:phenol is in general not critical; a condition is merely that a dispersion which can be readily and thoroughly mixed is obtained. For example, 1 to 2 parts by weight of water are employed per part by weight of phenol for preparation of the dispersion.

The reaction mixture of diazo solution and dispersed phenol typically comprises 1 to 5, in particular 1.5 to 2, parts by weight of water per part by weight of azo compound which can be prepared.

The diazonium salt of the compound of the formula II and the phenol of the formula III are advantageously employed in approximately equimolar amounts, for example 0.9 to 1.1 mol of diazonium salt are used per mole of phenol. Preferably, however, the azo coupling in the process according to the invention is carried out with a slight excess of phenol, for example a 1–5 mol%, in particular 2–4 mol%, excess of dispersed phenol of the formula III.

Before the start of the reaction with the diazonium compound, the phenol dispersion is advantageously seeded with a small amount of the compound of the formula I to be synthesized, for example with 0.1 to 5% by weight, in particular 0.5 to 2% by weight, of the theoretical amount of product.

In the process according to the invention, the diazo solution is usually metered into the dispersion of phenol of the formula III, water and dispersant mixture, which has been initially introduced into the reaction vessel; the portion of the diazo solution which has not yet been metered in is preferably cooled further. The metering is advantageously carried out slowly with control of the temperature and while stirring. During the metering in, the temperature of the reaction mixture is in general kept in the range of 0°–60° C., in particular in the range of 30°–50° C. An emulsified phenol having a melting point above the temperature maintained during the metering in usually remains in emulsified form during this operation. The reaction is usually carried out in the presence of mineral acids, for example hydrochloric acid (HCl) or sulfuric acid ($H_2SO_4$). The pH of the reaction mixture remains below 2; if appropriate, the mixture can also be topped up with acid during the reaction. After the diazo solution and dispersed phenol have been combined completely, the reaction mixture is advantageously further stirred, for example for 1–4 hours; preferably, the temperature is increased somewhat, for example to 30°–70° C., in particular to 40°–60° C., towards the end of the reaction.

The temperature particularly preferably remains in the range of 20° to 60° C. during the entire coupling reaction.

Further working up of the mixture can be carded out by known methods, for example by filtering off the product and then washing and drying it.

The filtration is preferably carried out at elevated temperature, for example at the reaction temperature. If necessary, further purification operations, for example washing or recrystallization, can follow.

The 2-nitroanilines of the formula II and 2,4-disubstituted phenols of the formula III used as starting substances are known in most cases and can be prepared by known methods or analogously to such methods.

The compounds of the formula I obtained according to the invention can advantageously be employed for the preparation of benzotriazoles. The corresponding benzotriazoles are used as light stabilizers, as described, for example, in the patent specification U.S. Pat. No. 3,004,896.

The invention therefore also relates to a process for the preparation of compounds of the formula V

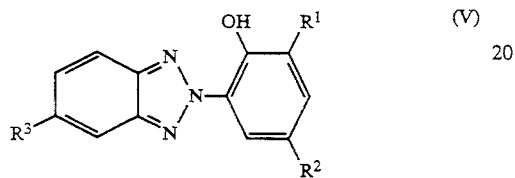

in which $R^1$ and $R^2$ independently of one another are $C_1-C_7$alkyl; and $R^3$ is hydrogen or halogen, by a) reaction of a diazonium salt of a 2-nitroaniline of the formula II

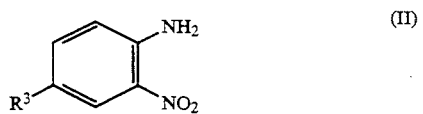

in acid aqueous solution with a phenol of the formula III

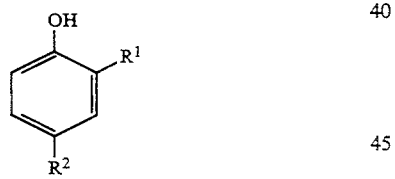

dispersed in water, to form the intermediate product of the formula I

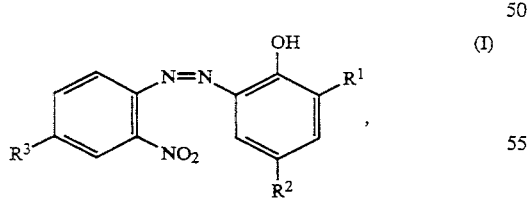

and b) subsequent reduction of the intermediate product of the formula I to form the compound of the formula V.

The process comprises employing as the dispersant in step (a) a $C_8-C_{20}$alkanesulfonic acid or a corresponding alkanesulfonate or a mixture of sulfonic acid and sulfonate together with a polyvinyl alcohol. Preferred radicals $R^1$ to $R^3$ and preferred embodiments of step (a) are as defined above.

The reaction conditions in step (b) of reductive cyclization of the substituted 2-nitro-2'-hydroxy-azobenzene are known in the art; publications in this context are, for example, U.S. Pat. No. 4,230,867, U.S. Pat. No. 4,642,350, U.S. Pat. No. 4,727,158, U.S. Pat. No. 4,999,433 and U.S. Pat. No. 5,187,289. Reducing agents which can be employed are, for example:

zinc, inter alia as a powder in alcoholic NaOH solution (U.S. Pat. No. 3,773,751; U.S. Pat. No. 4,727,158), zinc/ammonia or zinc/HCl (U.S. Pat. No. 2,362,988);

sulfides, such as alkali metal, ammonium or hydrogen sulfide (for example in U.S. Pat. No. 2,362,988);

alcohols, in particular primary and secondary alcohols in the presence of catalysts of the quinone or hydroquinone type and bases (for example U.S. Pat. No. 4,642,350);

hydrogen in the presence of transition metals, for example Ni, Ru, Rh, Pd or Pt, as catalysts, usually in activated form, for example as Raney nickel or on a support material such as, in the case of ruthenium, palladium or platinum, on charcoal (for example in U.S. Pat. No. 4,230,867; U.S. Pat. No. 4,999,433 and U.S. Pat. No. 5,187,289);

other methods are reduction with hydrazine and electrochemical reduction. The solvents used are usually alcohols, in particular lower alcohols, hydrocarbons or water, or corresponding binary or ternary mixtures. The reductions are usually carried out in an alkaline medium; bases which are often used are metal hydroxides, for example alkali metal hydroxides, such as NaOH or KOH, alkali metal carbonates, ammonia or amines, for example mono- or diethanolamine, di- or triethylamine, propylamine, butylamine or polyalkylenepolyamines, such as diethylenetriamine.

The following examples illustrate the process according to the invention further. Unless stated otherwise, all the data in parts or percentages in the examples and in the remainder of the description are by weight.

EXAMPLE 1

Preparation of 2-nitro-4-chloro-2'-hydroxy-3'-tert-butyl-5'-methyl-azobenzene

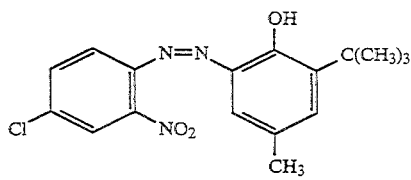

a) Preparation of the diazo solution 500 g of water and 0.5 g of sodium ligninsulfonate, as the dispersant, are initially introduced into a 3 liter flask with ground glass joints. 431.5 g of finely ground 4-chloro-2-nitroaniline are added, while stirring, and stirring is then continued for 30 minutes. 800 g of ice and 758 g of sulfuric acid (93%) are added. About 431 g of a 40% aqueous sodium nitrite solution are metered in at 15–18° C. (cooling) in the course of 2–2.5 hours. Complete reaction is checked by a control with acidified potassium iodide/starch paper (positive reaction for 30 minutes). The excess nitrite is then destroyed with 1–2 g of sulfamic acid and the solution is clarified by filtration.

b) Coupling reaction 770 g of water, 8.7 g of a partly acetylated polyvinyl alcohol (Mowiol® 8-88; molecular weight $M_w=49\,000$, residual acetyl content 10.7% by weight; manufacturer Hoechst A.G., Frankfurt a.M) and 17.4 g of a mixture of linear sodium $C_{13}$-$C_{17}$alkanesulfonates (Hostapur® SAS 93; manufacturer Hoechst A.G., Frankfurt a.M.) are initially introduced into a 5 liter flask. The dispersant mixture is dissolved at 60° C. in the course of about 30 minutes, while stirring. 422.8 g of molten 2-tert-butyl-4-methyl-phenol are then added in the course of 15 minutes, while stirring intensively (400 revolutions per minute), and the mixture is thoroughly mixed intensively for a further 15 minutes. It is then seeded with 9 g of coupling product, and the diazo solution prepared under (a), which is kept at 10°-15° C., is uniformly metered in at an internal temperature in the range of 34°-36° C. in the course of 5 hours. When the diazo feed has ended, the temperature is maintained for a further 2 hours, while stirring, and the mixture is then heated up 50° C. and kept at this temperature for 1 hour. The resulting suspension is filtered at about 50° C. and the solid is washed with 8 liters of water at 50° C. in portions. The filter cake is dried in a vacuum drying oven at 75°-80° C. 846 g of product having a content of 92.5% (determined by gas chromatography [GC]) and a melting range of 162-181 ° C. are thus obtained, corresponding to a yield of 90% of theory, calculated with respect to 4-chloro-2-nitroaniline, or 87.3% of theory, calculated with respect to 2-tert-butyl-4-methyl-phenol.

EXAMPLE 2

2-Nitro-4-chloro-2'-hydroxy-3',5'-di-tert-butyl-azobenzene

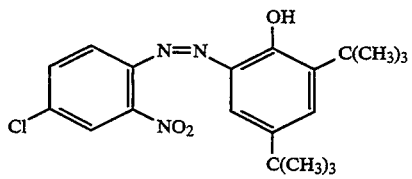

a) The preparation of the diazo solution is carried out as in Example 1a.

b) The coupling reaction is carried out in accordance with Example 1b, but 2 g of polyvinyl alcohol (Mowiol® 8-88) and 8 g of the mixture of linear sodium $C_{13}$-$C_{17}$alkanesulfonate (Hostapur® SAS 93) are used as the dispersant; 523.5 g of 2,4-di-tert-butyl-phenol are employed as the coupling component; the coupling temperature during the metered addition is in the range of 43°-45° C. The product is dried at 80°-85° C. under reduced pressure. 955 g of the title product with a content of 94% (GC) are obtained (melting point 194°-214° C.), corresponding to a yield of 92% of theory, calculated with respect to 4-chloro-2-nitroaniline.

If, instead of 2,4-di-tert-butyl-phenol, an equivalent amount of 2,4-di-tert-amyl-phenol or 2-sec-butyl-4-tert-butylphenol is employed under otherwise identical conditions, the following azo compounds are obtained:

2-nitro-4-chloro-2'-hydroxy-3',5'-di-tert-amyl-azobenzene or 2-nitro-4-chloro-2'-hydroxy-3'-sec-butyl-5'-tert-butyl-azobenzene.

EXAMPLE 3

2-(2'-Hydroxy-3',5'-di-tert-butylphenyl)-benzotriazole

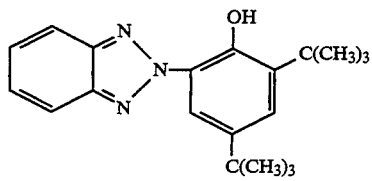

a) The preparation of the diazo solution is carried out in accordance with Example 1a, with the difference that 345.3 g of 2-nitroaniline are employed and the diazotization temperature is kept in the range from $-2°$ to $+2°$ C.

b) Coupling reaction to 2-Nitro-2'-hydroxy-3',5'-di-tert-butyl-azobenzene

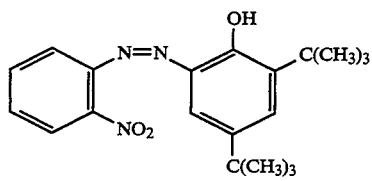

In accordance with Example 1b, with the following changes:

dispersant: 8.9 g of polyvinyl alcohol (Mowiol® 8-88) and 17.8 g of a mixture of branched sodium alkanesulfonate (Lutensit® A-PS; manufacturer BASF)

coupling component: 531.2 g of 2,4-di-tert-butyl-phenol temperature of the diazo solution in the dropping funnel: $-2°$ to $+2°$ C.

drying conditions: 75°-80° C./vacuum 888.5 g of the title product (b) of melting point 140°-145° C. with a content of 93% (GC) are obtained, the yield being 93% of theory, calculated with respect to 2-nitroaniline.

If, instead of 2,4-di-tert-butyl-phenol, an equivalent amount of 2-sec-butyl-4-tert-butylphenol or 2-tert-butyl-4-sec-butylphenol is employed under otherwise identical conditions, the following azo compounds are obtained:

2-nitro-2'-hydroxy-3'-sec-butyl-5'-tert-butylazobenzene;

2-nitro-2'-hydroxy-3'-tert-butyl-5'-sec-butylazobenzene.

c) Reduction to 2-(2'-Hydroxy-3',5'-di-tert-butylphenyl)-benzotriazole: 64.5 g of the above product (b), 2.2 g of a catalyst containing 5% Pt on carbon and 50% water, 64 g diethylenetriamine and 43 g xylene are initially introduced into a 300 ml autoclave. Air is removed and the mixture is stirred under constant 10 bar of hydrogen pressure at 50° C. until the reaction ends, which is after ca. 1 hour. Subsequently, the mixture is heated to 90° C., hydrogen is replaced by argon and the catalyst is filtered off. The aqueous phase is separated and the xylene phase washed twice with water. A part of the xylene is distilled off and replaced by methanol. After cooling to 0° C. the crystalline product is filtered off and washed with methanol. 52.2 g of the title product of 95% purity are obtained.

EXAMPLE 4

2-Nitro-2'-hydroxy-3',5'-di-tert-amyl-azobenzene

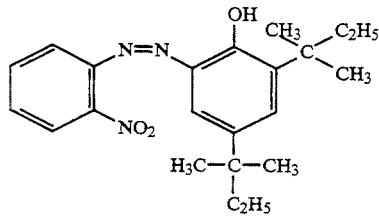

a) The preparation of the diazo solution is carried out in accordance with Example 1a, with the difference that 345.3 g of 2-nitroaniline are employed and the diazotization temperature is kept in the range of −2° to +2° C.

b) Coupling reaction: In accordance with Example 1b, with the following changes:
- dispersant: 9.6 g of polyvinyl alcohol (Mowiol® 8-88) and 19.2 g of linear alkanesulfonate (Hostapur® SAS 93)
- coupling component: 603.6 g of 2,4-di-tert-amylphenol
- temperature during metering in: 36°-38° C.
- temperature of the diazo solution in the dropping funnel: −2° to +2° C.
- drying conditions: 60°-65° C./vacuum 945 g of the title product of melting point 118°-126° C. with a content of 94% (GC) are obtained, the yield being 92.7% of theory, calculated with respect to 2-nitroaniline.

What is claimed is:

1. A process for the preparation of a compound of the formula I

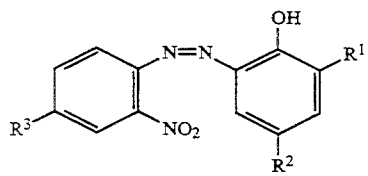

in which $R^1$ and $R^2$ independently of one another are $C_1$–$C_7$alkyl; and $R^3$ is hydrogen or halogen, by reaction of a diazonium salt of a 2-nitroaniline of the formula II

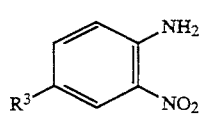

in acid aqueous solution with a phenol of the formula III

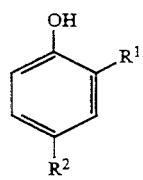

dispersed in water, in which the radicals $R^1$ to $R^3$ are as defined in formula I, which comprises employing as the dispersant a $C_8$–$C_{20}$alkanesulfonic acid and/or a corresponding alkanesulfonate together with a polyvinyl alcohol.

2. A process according to claim 1, in which $R^1$ and $R^2$ independently of one another are $C_1$–$C_5$alkyl; and $R^3$ is hydrogen or chlorine.

3. A process according to claim 2, in which $R^1$ and $R^2$ independently of one another are methyl or branched $C_3$–$C_5$alkyl.

4. A process according to claim 1, wherein an alkanesulfonic acid and/or the sodium or potassium salt thereof together with a polyvinyl alcohol of molecular weight 10,000 to 250,000 are employed as the dispersant.

5. A process according to claim 1, wherein the alkanesulfonic acid or alkanesulfonate is employed in an amount of 0.5 m 10% by weight and the polyvinyl alcohol is employed in an amount of 0.1 to 5% by weight, in each case based on the theoretical amount of azo compound of the formula I.

6. A process according to claim 5, wherein the dispersant comprises 1 to 20 parts by weight of polyvinyl alcohol per 10 parts by weight of alkanesulfonic acid and/or alkanesulfonate.

7. A process according to claim 1, wherein the alkanesulfonic acid or alkanesulfonate is derived from a straight-chain alkane.

8. A process according to claim 1, wherein the temperature is kept in the range of 20° to 60° C. throughout the entire coupling reaction.

9. A process according to claim 1, wherein the phenol of the formula III is employed in a 1 to 5% molar excess over the 2-nitroaniline of the formula II.

10. A process for the preparation of a compound of the formula V

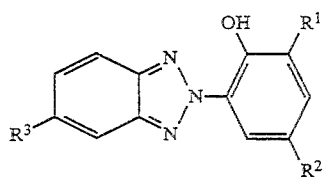

in which $R^1$ and $R^2$ independently of one another are $C_1$–$C_7$alkyl; and $R^3$ is hydrogen or halogen, by
a) reaction of a diazonium salt of a 2-nitroaniline of the formula II

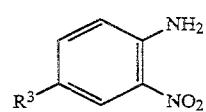

in acid aqueous solution with a phenol of the formula III

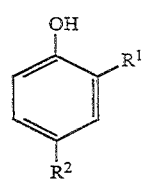

dispersed in water, to form the intermediate product of the formula I

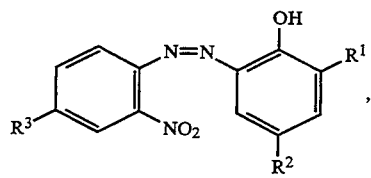
(I)
and
b) subsequent reduction of the intermediate product of the formula I to form the compound of the formula V,
which comprises employing as the dispersant in step (a) a $C_8$–$C_{20}$alkanesulfonic acid or a corresponding alkanesulfonate or a mixture of sulfonic acid and sulfonate together with a polyvinyl alcohol.
* * * * *